United States Patent
Jacobs, III et al.

(10) Patent No.: US 9,499,498 B2
(45) Date of Patent: Nov. 22, 2016

(54) PROCESS FOR THE PREPARATION OF TRIAZINE CARBAMATES

(71) Applicant: ALLNEX IP S.À.R.L., Luxembourg (LU)

(72) Inventors: William Jacobs, III, Bethel, CT (US); Lawrence A. Flood, Norwalk, CT (US)

(73) Assignee: ALLNEX IP S.À.R.L., Luxembourg (LU)

( * ) Notice: Subject to any disclaimer, the term of this patent is extended or adjusted under 35 U.S.C. 154(b) by 0 days.

(21) Appl. No.: 14/765,618

(22) PCT Filed: Feb. 28, 2014

(86) PCT No.: PCT/EP2014/053983
§ 371 (c)(1),
(2) Date: Aug. 4, 2015

(87) PCT Pub. No.: WO2014/135463
PCT Pub. Date: Sep. 12, 2014

(65) Prior Publication Data
US 2015/0376148 A1 Dec. 31, 2015

Related U.S. Application Data

(60) Provisional application No. 61/772,662, filed on Mar. 5, 2013.

(51) Int. Cl.
| | |
|---|---|
| *C07D 251/70* | (2006.01) |
| *C07D 251/24* | (2006.01) |
| *C07D 251/18* | (2006.01) |
| *C07D 251/22* | (2006.01) |

(52) U.S. Cl.
CPC .......... *C07D 251/24* (2013.01); *C07D 251/18* (2013.01); *C07D 251/22* (2013.01); *C07D 251/70* (2013.01)

(58) Field of Classification Search
CPC ..................................................... C07D 251/70
USPC .................................................. 544/196, 200
See application file for complete search history.

(56) References Cited

U.S. PATENT DOCUMENTS 5,705,641 A     1/1998  Flood et al.

FOREIGN PATENT DOCUMENTS

DE       102 18 617       11/2003

OTHER PUBLICATIONS

International Seach Report isued Apr. 28, 2014 in International (PCT) Application No. PCT/EP2014/053983.

*Primary Examiner* — Venkataraman Balasubramanian
(74) *Attorney, Agent, or Firm* — Wenderoth, Lind & Ponack, L.L.P.

(57) ABSTRACT

This invention relates to a process for the preparation of triazine carbamates by reacting a mixture of an aminotriazine A having at least two amino groups per molecule, an organic carbonate C which is preferably an acyclic carbonate, and a mixture B of bases comprising at least two basic metal compounds B1 and B2 individually selected from the group consisting of hydrides, amides, alkoxides, and arylalkoxides of metals, wherein the metal in B1 is not the same as the metal in B2.

14 Claims, No Drawings

PROCESS FOR THE PREPARATION OF TRIAZINE CARBAMATES

FIELD OF THE INVENTION

This invention relates to a process to prepare triazine carbamates by reacting aminotriazines and organic carbonates in the presence of basic metal compounds.

BACKGROUND OF THE INVENTION

A process for the preparation of a carbamate-functional triazine has been known from U.S. Pat. No. 5,705,641. This process involves reacting an aminotriazine having at least two amino groups, with an acyclic organic carbonate, in the presence of a base. Useful bases are listed as "alkali metal hydrides, alkali metal alkoxides, alkali metal hydroxides, alkali metal oxides, alkali metal carbonates, quaternary ammonium alkoxides, quaternary ammonium hydroxides, quaternary phosphonium alkoxides, quaternary phosphonium hydroxides, tertiary amines and mixtures thereof. Sodium and potassium alkoxides are most preferred, and include linear, branched and cyclic alkyl group containing alkoxides and mixtures thereof". While there is a general allusion to mixtures, the mandatory presence of bases from at least two different metals is not disclosed, and not exemplified in any of the examples.

It has been found in the experiments on which the present invention is based that excessively high viscosity occurs during the reaction which leads to excessive energy consumption for homogenisation during the reaction, and either the need to use special equipment such as thin film reactors or kneaders, or to the use or more diluted reaction mixtures with the consequent loss in space-time yield. It has therefore been desired to reduce the viscosity of the reaction mixture without having to resort to lower concentrations, or having to use special equipment. Reduced viscosity allows to increase the concentration of the desired product in the reaction mixture, thus also increasing space-time yield, and avoiding product losses.

SUMMARY OF THE INVENTION

It has been discovered in the experiments on which the present invention is based that the use of mixtures of bases made from different metals drastically reduces the viscosity of the reaction mixture.

The invention relates therefore to a process for the preparation of triazine carbamates by reacting a mixture of
an aminotriazine A having at least two amino groups per molecule,
an organic carbonate C, and
a mixture B of bases comprising at least two basic metal compounds B1 and B2 individually selected from the group consisting of hydrides, amides, alkoxides, and arylalkoxides of metals, wherein the metal in B1 is not the same as the metal in B2.

DETAILED DESCRIPTION OF THE PREFERRED EMBODIMENTS

The process of this invention may be conducted at a temperature of from −40° C. up to 150° C., preferably from 20° C. to 120° C. It is possible to charge first the aminotriazine component, A, and then adding concurrently or sequentially, the mixture B of bases comprising at least two basic metal compounds B1 and B2, and the organic carbonate C. It is also possible to charge a mixture of aminotriazine A, and organic carbonate C, and then adding the base to initiate the reaction. The preferred way is to initially charge the mixture B of bases, preferably in a solvent, and then to add jointly or consecutively, the aminotriazine A and the organic carbonate C.

The reaction may be conducted in a stoichiometric excess of the organic carbonate C over the aminotriazine A, which organic carbonate C may serve as solvent or diluent, and where the excess of organic carbonate C is removed after completion of the reaction, and neutralisation of the mixture B of bases, preferably by distillation. It is also possible, in a preferred way, to conduct the reaction in a solvent which is inert under the reaction conditions, such as an alcohol, a ketone, an ether, or a hydrocarbon solvent, or mixtures of these. It is preferred to use an alcohol or a mixture comprising an alcohol as solvent, particularly preferably comprising at least a mass fraction of 30% of the alcohol that corresponds to the metal alkoxide if a metal alkoxide is used as base.

The aminotriazine A has at least two primary amino groups, and may be selected from the group consisting of melamine, formoguanamine, acetoguanamine, benzoguanamine and caprinoguanamine, and from an N-alkylmelamine, and an N,N-dialkylmelamine, in which the alkyl groups may be the same or may be different, and the alkyl groups may individually have from one to twenty carbon atoms, and may be linear or branched (if the number of carbon atoms is three or more) or cyclic (if the number of carbon atoms is three or more). Particularly preferred are melamine, acetoguanamine, and benzoguanamine.

The mixture B of bases comprises at least two different basic compounds B1 and B2 which are derived from metals. It is mandatory that at least the metal M1 of the basic compound B1=M1 X1 where X1 is the anion of the basic compound B1, and M1 is the cation of the basic compound B1, is different from the metal M2 of the basic compound B2=M2 X2 where X2 is the anion of the basic compound B2, and M2 is the cation of the basic compound B2, in order to reduce the viscosity of the reaction mixture to the desired level. Therefore, the mixture B of bases preferably comprises a mixture of at least two bases B1 and B2 containing the same anion, and at least two different cations. If more than two basic compounds are used, such that the mixture B of bases comprises three or more basic compounds B1, B2, and B3, and optionally B4 etc., the metal M3 which is comprised in the basic compound B3=M3 X3, may be the same as M1 or the same as M2, in which case the anions X1 or X2 are different from X3, or may M3 be different from both M1 and M2. Likewise, for four basic compounds B1, B2, B3, and B4, any of the metals M3 and M4 which are comprised in the basic compounds B3=M3 X3, and B4=M4 X4 may be the same as M1 or the same as M2, in which case the anions X1 or X2 are different from X3 and X4, respectively, or at least one of the metals M3 and M4 may be different from both M1 and M2. It is therefore only needed that at least two different metals are comprised in the mixture B of bases. The use of three basic compounds B1, B2, B3 each being derived from different metals M1, M2 and M3 where each metal is different from the other two further reduces the viscosity of the reaction mixture. Using more than three basic compounds still further reduces the viscosity of the reaction mixture.

The mixture B of bases preferably comprises at least two different basic metal compounds B1 and B2 which are derived from alkali or earth alkali metals. It is preferred to use bases derived from different alkali or earth alkali metals, i. e. the metals M1 and M2 are independently of each other selected from the group consisting of alkali metals, and earth alkali metals, and they may not be the same. The further metals M3, M4, etc. may also be independently of each other selected from the group consisting of alkali metals, and earth alkali metals. As it had been found that the presence of lithium derived bases or of magnesium derived bases had a particularly pronounced effect on the reduction of viscosity of the reaction mixture, it is particularly preferred that either lithium or magnesium, or both, particularly in the case of a mixture of bases derived form three or more different metals, are present as the metals M1 or M2. If three different bases are used, the presence of either lithium or magnesium lowers the viscosity markedly, such as in a combination of bases where one is derived from sodium, another from potassium, and a third from lithium or from magnesium. Therefore, the mixture B of bases comprises in this preferred case a basic lithium compound or a basic magnesium compound, or both a basic lithium compound and a basic magnesium compound. The viscosity is reduced even more if both lithium and magnesium are present, such as in a combination of lithium-, magnesium-, and sodium-derived bases. Therefore, it is further preferred that both lithium and magnesium are used as metals constituting these bases, and it is further preferred that in this case, sodium or potassium are used as other metals.

Preferred anions are alkoxides. Particularly preferred combinations are therefore mixtures of lithium alkoxides and sodium alkoxides, mixtures of lithium alkoxides and potassium alkoxides, mixtures of lithium alkoxides, potassium alkoxides and sodium alkoxides, mixtures of magnesium alkoxides and sodium alkoxides, mixtures of magnesium alkoxides and potassium alkoxides, mixtures of magnesium alkoxides, potassium alkoxides and sodium alkoxides, mixtures of lithium alkoxides, magnesium alkoxides, and sodium alkoxides, as well as mixtures of lithium alkoxides, magnesium alkoxides, and potassium alkoxides.

It has also been found that lithium alkoxides and magnesium alkoxides if used alone, i. e., not in mixture with further metal based bases, lead to very low viscosity reaction mixtures which makes these easily stirrable even in high concentrations of educts and products; however, reaction mixtures based on these single metal lithium alkoxides or magnesium alkoxides tend to solidify upon cooling after the reaction has been completed, to below 60° C. down to ambient temperature (25° C.). In these cases, a part of the alcohol-acid mixture needed for dilution and neutralisation of the base is preferably added at a temperature of at least 60° C. during the cooling of the fully reacted reaction mixture. This dissolves at least a part of the salt formed during the reaction, and reduces the propensity of the reaction mixture to solidify. Water may also be added to the neutralisation mixture to enhance the solubility of the salt.

The anions X1 and X2 may be the same, or may be different, in the at least two different basic compounds B1 and B2 wherein at least two different metals M1 and M2 are used, such as a mixture of sodium methoxide and potassium methoxide, or a mixture of sodium butoxide and lithium butoxide, or mixture of sodium hydride and potassium ethoxide, or a mixture of lithium methoxide and calcium bismethoxide. The preferred anions are alkoxides. A particularly high reduction of the viscosity of the reaction mixture has been noted when using alkoxides based on tertiary alcohols, such as tert.-butoxide, and the alkoxides derived from 2-methyl-2-hydroxybutane, 3-methyl-3-hydroxypentane, and 3-ethyl-3-hydroxy-pentane.

Particularly good viscosity reduction effect has thus been noted when using mixtures of lithium tert.-butoxide with sodium tert.-butoxide, mixtures of lithium tert.-butoxide with potassium tert.-butoxide, and mixtures of magnesium tert.-butoxide with sodium tert.-butoxide, or with potassium tert.-butoxide. Among the ternary mixtures, those comprising lithium tert.-butoxide, sodium tert.-butoxide, and potassium tert.-butoxide, and those comprising magnesium tert.-butoxide, sodium tert.-butoxide, and potassium tert.-butoxide, are especially preferred.

A preferred embodiment comprises an in-situ synthesis of the alkoxides from corresponding metals or metal compounds by heating a mixture of compounds of at least two different metals, and an alcohol having from one to six carbon atoms, optionally in the presence of an entrainment agent, wherein the metal compounds are individually selected from the group consisting of metal hydrides, metal oxides, metal hydroxides, metal amides, and organometal compounds. It is preferred, also in this context, that the metals are at least two metals selected from the group consisting of alkali and earth alkali metals. Preferably, the entrainment agent which is optionally used is an alkane having at least six carbon atoms, or an aromatic or alkylaromatic compound such as toluene or xylene. In a further preferred embodiment, the in-situ formation of alkoxides may be done in the same vessel where the reaction between the mixture B of bases, the aminotriazine A, and the organic carbonate C is to be conducted.

Particularly preferred as mixture B of bases are mixtures of at least two bases B1 and B2 containing the same anion, and at least two different metals M1 and M2 as cations.

The organic carbonate C has the structure $R^1O-CO-OR^2$, where $R^1$ and $R^2$ may be the same or may be different, and are individually selected from the group consisting of alkyl radicals having from one to twenty carbon atoms, and may be linear, or branched (if the number of carbon atoms is three or more) or cyclic (if the number of carbon atoms is three or more), or may together form an alkylene radical having from two to twenty carbon atoms, which may be linear or branched (if the number of carbon atoms is three or more) or cyclic (if the number of carbon atoms is three or more). Preferred are dimethyl carbonate, diethyl carbonate, di-n-propyl carbonate, di-isopropyl carbonate, di-n-butyl carbonate, di-sec. butyl carbonate, di-isobutyl carbonate, and di-tert. butyl carbonate. It is also possible to use cyclic carbonates such as ethylene carbonate, 1,2-propylene carbonate, and 1,3-propylene carbonate, or their mixtures, or also mixtures of cyclic carbonates and carbonates of formula $R^1O-CO-OR^2$ supra.

Avoidance of high viscosity reaction intermediates that are encountered with the base and carbonate processes known from the patent literature allows to use much higher reaction concentrations and thus significant improvements in product throughput and space-time-yield. The process of this invention also allows to utilise conventional reactor designs with conventional stirrer configurations, while in the processes known from the patent literature, large amounts of solvents are needed to prevent clogging and adhesion of the reaction mass to the stirrer in a conventional reactor set-up. While in the base carbonate processes used hithertofore, the encountered high intermediate reaction viscosities dictated that the product concentrations (mass fraction of triazine carbamate in the reaction mixture after completion of the reaction) could be no higher than from 10% to 15% in order for the reaction mixture to be fluid enough for stirring, the process of this invention allows to increase reaction product concentrations such as by a factor of three or more compared to a process using a single alkali alkoxide base such as sodium methoxide, while maintaining efficient stirring.

The triazine carbamates that are prepared by the process of this invention can be used to form crosslinked coatings, inks, adhesives, sealants, composites, laminates, sizings for textiles and carbon fibers, binders for paper and particle board, as well as numerous other thermosetting applications when heated with suitable polymeric or oligomeric backbone materials for a sufficient time and temperature to effect cure. The suitable polymeric or oligomeric backbone materials have the appropriate reactivity and functional groups to react with said triazine carbamate crosslinker composition with or without a catalyst, to form a crosslinked network after curing. The resulting composition can be applied to the substrate in the typical manner such as spraying, dipping, roller coating, brushing, etc. These compositions are particularly suitable for durable, light stable coatings useful for automotive topcoats and other UV stable outdoor applications requiring high durability.

The invention is further explained in the following examples which are not to be construed as limiting.

The following expressions are used in the examples, and also in the specification, with the meanings as defined herein:

"Strength" stands for a mass fraction, particularly used in aqueously diluted acids or bases, where, e.g. "50% strength sulphuric acid" refers to an aqueous dilution of sulphuric acid with a mass fraction of 50% of $H_2SO_4$ in the diluted acid.

Dynamic viscosity is measured with a cone and plate rotation viscometer, at 23° C. or 90° C. or 100° C., as stated, and a shear rate of 100 $s^{-1}$ if not stated differently.

Example 1

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added under stirring 426.2 g of deaerated n-butanol, 48.1 g of anhydrous sodium tert.-butoxide, 27.0 g of anhydrous lithium tert.-butoxide and 6.2 g of lithium methoxide. The temperature of the mixture rose to 57° C. whereupon 31.5 g of melamine and 72.5 g of dimethylcarbonate were added with stirring. With continued stirring the white slurry was then heated to 90° C. Within thirty minutes at 90° C. the reaction mixture became clear, light yellow and virtually water thin, the viscosity was measured as between 5 mPa·s and 10 mPa·s at this point. The clear reaction mixture was held at 90° C. for an additional hour and was then cooled to from 20° C. to 25° C. To the same reactor, with good stirring and cooling, was slowly added a room temperature (23° C.) solution of 50.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction mixture was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by High Pressure Liquid Chromatography (HPLC) and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl-, bis-methyl- and mixed n-butyl-methyl-carbamoyl-1,3,5-s-triazine, including traces of mono-n-butylcarbamoyl-1,3,5-s-triazine and mono-methyl-carbamoyl-1,3,5-s-triazine.

Comparative Example 1

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine utilising a single metal base process To a suitable three necked flask ("reactor 1"), equipped with a reflux condenser, an equal pressure addition funnel, a mechanical stirrer, a heating mantle and an inlet for a dry nitrogen atmosphere were added with stirring 480.12 g of deaerated solution of sodium n-butoxide in n-butanol having a mass fraction of solids of 20%, 31.5 g of melamine and 72.5 g of dimethylcarbonate with a dry nitrogen sparge. Under continued stirring the white slurry was then heated to 90° C. Within thirty minutes at 90° C., the reaction mixture became extremely viscous, taking on the appearance of foamed shaving cream (having a viscosity of approximately 100 Pa·s at this point. The thick reaction mixture which partially adhered to the stirrer was held at 90° C. for an additional hour and was then cooled to from 20° C. to 25° C. To a second reactor ("reactor 2"), with good stirring, 40.0 g of concentrated sulfuric acid were slowly added to 66.4 g of deaerated n-butanol with good cooling such that the temperature did not exceed 10° C. during solution preparation. After complete addition of the sulfuric acid to the n-butanol in reactor 2, the thick slurry of the tri-sodium salt of alkylcarbamoyl-1,3,5-s-triazine of reactor 1 was transferred slowly in portions to reactor 2 under good stirring and cooling, keeping the temperature below 35° C. during the addition. In repetition of this comparative experiment, losses of about 20% to 25% were typically observed due to material that could not be removed from reactor 1 and the stirrer, during transfer at this neutralisation step. After addition of the slurry was complete, the final pH of the reaction mixture (measured as supra on a dilution of 1 g of reaction mixture sample in 2 g of water) was adjusted to a pH value between 4.5 and 5.0 with further solution of anhydrous sulfuric acid in n-butanol. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methylcarbamoyl-1,3,5-s-triazine with a small amount of the bis-n-butyl- and bis-n-methyl- and mixed n-butyl-methyl-carbamoyl-1,3,5-s-triazine including traces of mono-n-butyl-carbamoyl-1,3,5-s-triazine and mono-methylcarbamoyl-1,3,5-s-triazine. In a series of ten similar experiments of each example 1 and comparative example 1, the yield of solid product from this process averaged about 20% lower than that from the process of this invention at equally charged initial reagent molar concentrations.

Example 2

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added with stirring 426.2 g of deaerated n-butanol, 56.1 g of anhydrous potassium tert.-butoxide and 48.1 g of anhydrous lithium tert.-butoxide. The temperature of the mixture rose to 60° C. whereupon 31.5 g of melamine and 72.5 g of dimethylcarbonate were added under stirring. With continued stirring, the white slurry was then heated to 90° C. Within thirty minutes at 90° C., the reaction mixture became clear, light yellow and virtually water thin (the viscosity was between 3 mPa·s to 5 mPa·s at this point in five runs of this same experiment). The clear reaction mixture was held at 90° C. for an additional hour and was then cooled to from 20° C. to 25° C. To the same reactor, with good stirring and cooling, was slowly added a room temperature (23° C.) solution of 50.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methylcarbamoyl-1,3,5-s-triazine with a small amount of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

Example 3

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added with stirring 426.2 g of deaerated n-butanol, 37.5 g of anhydrous potassium tert.-butoxide, 32.1 g of anhydrous sodium tert.-butoxide and 12.7 g of anhydrous lithium methoxide. The temperature of the mixture rose to 56° C. whereupon 31.5 g of melamine and 72.5 g of dimethylcarbonate were added under stirring. With continued stirring the white slurry was then heated to 90° C. Within thirty minutes at 90° C., the reaction mixture became a translucent, light yellow solution and was virtually water thin (the viscosity was between 5 mPa·s to 10 mPa·s at this point in five runs of this same experiment). The reaction mixture was held at 90° C. for an additional hour and was then cooled to from 20° C. to 25° C. To the same reactor, with good stirring and cooling, was slowly added a room temperature solution of 50.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methylcarbamoyl-1,3,5-s-triazine including traces of mono-n-butylcarbamoyl-1,3,5-s-triazine and mono-methylcarbamoyl-1,3,5-s-triazine.

Example 4

Typical Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added under stirring 426.2 g of deaerated n-butanol, 48.1 g of anhydrous sodium tert.-butoxide and 47.4 g of anhydrous magnesium tert.-butoxide. The temperature of the mixture rose to 54° C. whereupon 31.5 g of melamine and 72.5 g of dimethylcarbonate were added under stirring. With continued stirring, the greenish coloured slurry was then heated to 100° C. Within thirty minutes at 100° C., the reaction mixture became a light yellow hazy mixture and was very fluid (the viscosity was between 2 mPa·s to 50 mPa·s at this point in five runs of this same experiment). The reaction mixture was held at 100° C. for an additional thirty minutes and was then cooled to from 20° C. to 25° C. To the same reactor, with good stirring and cooling, was slowly added a room temperature (23° C.) solution of 50.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

Example 5

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added under stirring 426.2 g of deaerated n-butanol, 48.1 g of anhydrous sodium tert.-butoxide and 28.4 g of anhydrous calcium methoxide. The temperature of the mixture rose to 43° C. whereupon 31.5 g of melamine and 72.5 g of dimethylcarbonate were added under stirring. With continued stirring, the white coloured slurry was then heated to 90° C. The reaction mixture was held at 90° C. for two hours (the viscosity was between 150 mPa·s and 250 mPa·s at this point in five runs of this same experiment) and was then cooled to from 20° C. to 25° C. To the same reactor, with good stirring and cooling, was slowly added a room temperature solution of 50.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

Example 6

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser, an equal pressure addition funnel, a mechanical stirrer, a heating mantle and an inlet for a dry nitrogen atmosphere were added under stirring 301.4 g of deaerated n-butanol, 15.5 g of anhydrous potassium tert.-butoxide, 66.4 g of anhydrous sodium tert.-butoxide and 26.3 g of anhydrous lithium methoxide. The temperature of the mixture rose to 63° C. whereupon 43.5 g of melamine and 100.1 g of dimethylcarbonate were added under stirring. With continued stirring the white slurry was then heated to 100° C. Within thirty minutes at 100° C., the reaction mixture became a translucent, light yellow hazy solution and remained very fluid (the viscosity was between 10 mPa·s and 50 mPa·s at this point in five runs of this same experiment). The reaction mixture was held at 100° C. for an additional thirty minutes and was then cooled to from 20° C. to 25° C. Although the reaction mixture thickened in this temperature range, it was still easily stirred (the viscosity was between 1 Pa·s and 10 Pa·s at this point in five runs of this same experiment), allowing neutralisation in the same vessel. Therefore, to the same reactor, with good stirring and cooling, was slowly added a room temperature (23° C.) solution of 69.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analyzed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

Example 7

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask ("reactor 1"), equipped with a reflux condenser, an equal pressure addition funnel, a mechanical stirrer, a heating mantle and an inlet for a dry nitrogen atmosphere were added under stirring 301.4 g of deaerated n-butanol, 96.1 g of anhydrous sodium tert.-butoxide and 38.0 g of anhydrous lithium methoxide. The temperature of the mixture rose to 61° C. whereupon 56.8 g of melamine and after a delay of fifteen minutes, 130.6 g of dimethylcarbonate were added under stirring. With continued stirring, the white slurry was then heated to 100° C. Within thirty minutes at 100° C., the reaction mixture became a translucent, light yellow hazy solution and remained very fluid (the viscosity was between 50 mPa·s and 100 mPa·s at this point in five runs of this same experiment). The reaction mixture was held at 100° C. for an additional thirty minutes and was then cooled to from 55° C. to 60° C. and maintained at that temperature. To a second reactor ("reactor 2") was slowly added 90.0 g of concentrated sulfuric acid to 66.4 g of deaerated n-butanol with vigorous stirring and cooling such that the temperature did not exceed 10° C. during solution preparation. After complete addition of the sulfuric acid to the n-butanol in reactor 2, the heated solution of the mixed salts of alkylcarbamoyl-1,3,5-s-triazines in reactor 1 was transferred slowly to reactor 2, keeping the temperature in reactor 2 below 35° C. during the addition. After addition of the reaction mixture from reactor 1 was complete, the final pH of the product mixture in reactor 2 was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methylcarbamoyl-1,3,5-s-triazine including traces of mono-n-butylcarbamoyl-1,3,5-s-triazine and mono-methylcarbamoyl-1,3,5-s-triazine.

Example 8

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable three necked flask, equipped with a reflux condenser having a decanting trap in the distillate return line, an equal pressure addition funnel, a mechanical stirrer, a heating mantle and an inlet for a dry nitrogen atmosphere were added under stirring 301.4 g of deaerated n-butanol, 7.7 g of potassium hydroxide prills, 27.6 g of sodium hydroxide prills and 16.6 g of anhydrous lithium hydroxide powder. To the decanting trap in the distillate return line were added 88.3 g of n-heptane, completely filling the trap and allowing the excess to flow into the reactor. The well stirred reaction mixture was then brought to vigorous reflux and the water of reaction that collected in the decanting trap was monitored. When a fraction of 90% to 95% of the theoretical amount of water was collected in the trap, the water was drained and the reaction mixture was cooled to from 35° C. to 40° C. To the well stirred reaction mixture were then added 43.5 g of melamine and 100.1 g of dimethylcarbonate. With continued stirring the white slurry was then heated to 100° C., and within thirty minutes the reaction mixture became a translucent, light yellow hazy solution and remained very fluid (the viscosity was between 10 mPa·s and 50 mPa·s at this point in five runs of this same experiment). The reaction mixture was held at 100° C. for an additional thirty minutes and was then cooled to from 20° C. to 25° C. Although the reaction mixture thickened in this temperature range, it was still easily stirred (the viscosity was between 1 Pa·s and 10 Pa·s at this point in five runs of this same experiment), allowing neutralisation in the same vessel. Therefore, to the same reactor, with good stirring and cooling, was slowly added a room temperature (23° C.) solution of 69.0 g of sulfuric acid in 66.4 g of deaerated n-butanol such that the temperature did not exceed 35° C. during the addition. The solution of sulfuric acid in deaerated n-butanol was previously prepared by carefully adding the concentrated sulfuric acid to deaerated n-butanol with vigorous stirring and cooling. After complete addition, the final pH of the reaction was adjusted to a pH value between 4.5 and 5.0 by addition of further solution of anhydrous sulfuric acid in n-butanol as described supra, with pH measurements on the reaction mass being performed on a mixture of 1 g of reaction mixture sample with 2 g of water. The reaction mixture was then filtered free of salts and the solution of product was then analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

Example 9

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine The reaction process as in Example 8 was repeated in all respects except, to the decanting trap in the distillate return line was added 88.3 g of n-octane (instead of n-heptane), completely filling the trap and allowing the excess to flow into the reactor. The use of n-octane allowed for a faster, and a more efficient removal of the water of reaction from the reaction mixture. The final product was similar in quantity and quality to that of Example 8.

Example 10

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine To a suitable reactor ("reactor 1"), equipped with a condenser for distillation or reflux and having a decanting trap in the distillate return line, a portal for the addition of solids, a pumping system for the addition of liquids, a mechanical stirrer suitable for good agitation, a heating and cooling system and an inlet for a dry nitrogen atmosphere were added with stirring 301.4 g of deaerated n-butanol, 36.0 g of sodium hydroxide, 21.6 g of anhydrous lithium hydroxide and 0.04 g sodium borohydride. To the decanting trap in the distillate return line were added 85.6 g of n-heptane, completely filling the trap and allowing the excess to flow into the reactor. The well stirred reaction mixture was then brought to vigorous reflux and the water of reaction that collected in the decanting trap was monitored. After about five and one half hours when approximately 96% of theoretical amount of water was collected, the water was drained and the majority of the added heptane was removed at atmospheric pressure (about 87 g by the volume of distillate). The reaction mixture was then cooled to 70° C. and then, 43.5 g of melamine and 130.6 g of deaerated dimethylcarbonate was added. With continued stirring the white slurry was then heated to 90° C. and within thirty minutes, the reaction mixture became a translucent, light yellow hazy solution and remained very fluid. The reaction mixture was held at 90° C. for an additional thirty minutes and was then cooled to from 55° C. to 60° C. To a second reactor ("reactor 2") under a nitrogen atmosphere, 260.0 g of deionised water were added which was then cooled to 10° C. under stirring. To the cold water in reactor 2 were slowly added 145.8 g of aqueously diluted nitric acid having a mass fraction of 70% of $HNO_3$, keeping the temperature below 15° C. during the addition. After complete addition of the nitric acid to the water in reactor 2, the heated solution of the mixed salts of alkylcarbamoyl-1,3,5-s-triazines from reactor 1 was metered slowly into reactor 2, keeping the temperature in reactor 2 below 35° C. during the addition. After addition of the reaction mixture from reactor 1 was complete, the final pH of the product mixture in reactor 2 was adjusted to pH value of from 4.5 to 5.0 with aqueously diluted nitric acid having a mass fraction of 70% of $HNO_3$. The reaction mixture was then agitated for an additional fifteen minutes and then the agitation was stopped, allowing the aqueous layer and the organic layer to phase separate. After phase separation the aqueous layer was drained off and the organic layer was washed twice with deionised water the volume of which was one quarter of the total organic volume, draining off the aqueous layer between each wash. The organic solution of product was then concentrated by removal of volatiles under reduced pressure at 40° C., adjusting the pressure accordingly to maximise distillation rates. The end point of the strip was monitored by comparison of the refractive index of a standard solution of the product in n-butanol having a mass fraction of solids of 50% with the contents of the reactor versus stripping time. The final product was analysed by HPLC and mass spectrometry and shown to be mainly 2,4,6-tris-n-butyl- and 2,4,6-tris-methyl- and mixed 2,4,6-tris-n-butyl-methyl-carbamoyl-1,3,5-s-triazine with a small amount of the bis-n-butyl- and bis-methyl- and mixed butyl-methyl-carbamoyl-1,3,5-s-triazine including traces of mono-n-butylcarbamoyl-1,3,5-s-triazine and mono-methylcarbamoyl-1,3,5-s-triazine in organic solution, having mass fraction of solids of between 49% and 52%.

Example 11

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine using utilising a single metal base process (Lithium alkoxide)

To a suitable four-necked flask, equipped with a reflux condenser, an equal pressure addition funnel, a mechanical stirrer, a heating mantle, a thermocouple and an inlet for a dry nitrogen atmosphere were added with stirring 301.6 g of deaerated n-butanol and 58.7 g of anhydrous lithium tert.-butoxide. The temperature of the mixture rose to 42° C. whereupon 22.4 g of melamine and 51.5 g of dimethylcarbonate were added under stirring. With continued stirring (262 min$^{-1}$), the white slurry was then heated to 90° C. Within thirty minutes at 90° C., the reaction mixture became very light yellow, slightly hazy and virtually water thin in viscosity (between 1 mPa·s and 5 mPa·s for five repetitions of the example). The reaction mixture was held at 90° C. for a full hour and was then cooled to 10° C. To the same reactor, with good stirring and cooling, was slowly added a chilled (4° C.) solution of 36.3 g of 96% strength sulfuric acid in 47.1 g of deaerated n-butanol such that the temperature did not exceed 20° C. during the addition. After complete addition, the final pH of the reaction was adjusted to a pH value between 4.5 and 5.0 by addition of further solution of 96% strength sulfuric acid in n-butanol as described supra, with pH measurements on the reaction mass being performed on a mixture of 3 g of reaction mixture sample with 3 g of water. The reaction mixture was then filtered free of salts and the solution of product was then analysed by HPLC, TLC, and C13 NMR and shown to be mainly 2,4,6-tris-n-butyl- and 2,4,6-tris-methyl- and mixed 2,4,6-tris-n-butyl-methylcarbamoyl-1,3,5-s-triazine with smaller amounts of the bis-n-butyl- and bis-methyl- and mixed n-butyl-methyl-carbamoyl-1,3,5-s-triazine including traces of mono-n-butylcarbamoyl-1,3,5-s-triazine and mono-methylcarbamoyl-1,3,5-s-triazine.

In a repetition of the example, the neutralisation solution comprising butanol and sulfuric acid was added under cooling starting at 90° C. down to room temperature (25° C.), where care was taken to keep the temperature of the reaction mixture under 100° C. during the addition. By this continuous addition and neutralisation, a rise in viscosity could be avoided.

Example 12

Synthesis of 2,4,6-Tris-Alkylcarbamoyl-1,3,5-s-Triazine, Bis-Alkylcarbamoyl-1,3,5-s-Triazine and Mono-Alkylcarbamoyl-1,3,5-s-Triazine using utilising a single metal base process (Magnesium alkoxide)

To a suitable four necked flask, equipped with a reflux condenser, an equal pressure addition funnel, a mechanical stirrer, a heating mantle, a thermocouple and an inlet for a dry nitrogen atmosphere were added with stirring 301.6 g of deaerated n-butanol and 67.3 g of anhydrous magnesium di-tert.-butoxide. The temperature of the mixture rose to 23° C. whereupon 22.4 g of melamine and 51.5 g of dimethylcarbonate were added under stirring. With continued stirring (262 min$^{-1}$), the light yellowish tan slurry was then heated to 90° C. Within thirty minutes at 90° C., the reaction mixture became light yellow, lightly hazy and virtually water thin in viscosity (between 1 mPa·s and 5 mPa·s for five repetitions of the example). The reaction mixture was held at 90° C. for a full additional hour and was then cooled to 10° C. To the same reactor, with good stirring and cooling, was slowly added a chilled (4° C.) solution of 38.0 g of 96% strength sulfuric acid in 50.0 g of deaerated n-butanol such that the temperature did not exceed 20° C. during the addition. After complete addition, the final pH of the reaction was adjusted to a pH value between 4.5 and 5.0 by addition of further solution of 96% sulfuric acid in n-butanol as described supra, with pH measurements on the reaction mass being performed on a mixture of 3 g of reaction mixture sample with 3 g of water. To the reaction mixture was then added 350 g of deionised water, stirred, and then allowed to phase split. The organic layer was separated and dried over anhydrous sodium sulphate and then filtered free of salts. The resulting solution of product was then analysed by HPLC, TLC, and C13 NMR and shown to be mainly a mixture comprising 2,4,6-tris-n-butyl- and mixed 2,4,6-tris-n-butyl-methylcarbamoyl-1,3,5-s-triazines, bis-n-butyl- and bis-methyl- and mixed n-butyl-methyl-carbamoyl-1,3,5-s-triazines and mono-n-butylcarbamoyl-1,3,5-s-triazine and mono-methylcarbamoyl-1,3,5-s-triazines.

In a repetition of the example, the neutralisation solution comprising butanol and sulfuric acid was added under cooling starting at 90° C. down to room temperature (25° C.), where care was taken to keep the temperature of the reaction mixture under 100° C. during the addition. By this continuous addition and neutralisation, a rise in viscosity could be avoided.

The invention claimed is:

1. A process for the preparation of a triazine carbamate comprising reacting a mixture of
   an aminotriazine A having at least two amino groups per molecule,
   an organic carbonate C, and
   a mixture B of bases comprising at least two basic metal compounds B1 and B2 individually selected from the group consisting of hydrides, amides, alkoxides, and arylalkoxides of metals, wherein the metal in B1 is not the same as the metal in B2,
   wherein the mixture B of bases comprises at least two different basic metal compounds B1 and B2 which are derived from alkali or earth alkali metals.

2. The process of claim 1 which is conducted at a temperature of from −40° C. up to 150° C.

3. The process of claim 1 wherein first, the mixture B of bases is charged, and then jointly or consecutively, the aminotriazine A and the organic carbonate C are added.

4. The process of claim 1 wherein first, the aminotriazine component, A, is charged and then, concurrently or sequentially, the mixture B of bases comprising at least two basic metal compounds B1 and B2, and the organic carbonate C, are added.

5. The process of claim 1 wherein the reaction is conducted in a solvent which is inert under the reaction conditions.

6. The process of claim 1 wherein the aminotriazine A has at least two primary amino groups, and may be selected from the group consisting of melamine, formoguanamine, acetoguanamine, benzoguanamine and caprinoguanamine, and from an N-alkylmelamine, and an N,N-dialkylmelamine, in which the alkyl groups may be the same or may be different, and the alkyl groups may individually have from one to twenty carbon atoms, and may be linear or branched, if the number of carbon atoms is three or more, or cyclic, if the number of carbon atoms is three or more.

7. The process of claim 1 wherein the mixture B of bases comprises metal alkoxides which are prepared in situ from corresponding metals or metal compounds by heating a mixture of compounds of at least two different metals, and an alcohol having from one to six carbon atoms, optionally in the presence of an entrainment agent, wherein the metal compounds are individually selected from the group consisting of metal hydrides, metal oxides, metal hydroxides, metal amides, and organometal compounds.

8. The process of claim 1 wherein the mixture B of bases comprises a mixture of at least two bases B1 and B2 containing the same anion, and at least two different cations.

9. The process of claim 1 wherein the mixture B of bases comprises a basic lithium compound or a basic magnesium compound, or both a basic lithium compound and a basic magnesium compound.

10. The process of claim 1 wherein the organic carbonate C has the structure $R^1O-CO-OR^2$, where $R^1$ and $R^2$ may be the same or may be different, and are individually selected from the group consisting of alkyl radicals having from one to twenty carbon atoms, and may be linear or branched if the number of carbon atoms is three or more, or cyclic if the number of carbon atoms is three or more, or may together form an alkylene radical having from two to twenty carbon atoms, and may be linear or branched if the number of carbon atoms is three or more or cyclic if the number of carbon atoms is three or more.

11. The process of claim 1 wherein the aminotriazine A is selected from the group consisting of melamine, acetoguanamine, and benzoguanamine.

12. The process of claim 1 wherein the organic carbonate is an acyclic carbonate.

13. The process of claim 3 wherein the mixture of bases is charged in a solvent.

14. The process of claim 5 wherein the solvent is selected from the group consisting of an alcohol, a ketone, an ether, a hydrocarbon solvent, and mixtures thereof.

* * * * *